United States Patent [19]

Takács et al.

[11] Patent Number: 4,518,771

[45] Date of Patent: May 21, 1985

[54] PROCESS FOR THE PRODUCTION OF HEPARIN-CONTAINING PARTICULATE PRODUCTS

[75] Inventors: István Takács; György Kerey; János Illés; Péter Rudolf; Pál Gere; László Czebe; Erzsébet Neszmélyi, all of Budapest, Hungary

[73] Assignee: Richter Gedeon Vegyeszeti Gyar RT., Budapest, Hungary

[21] Appl. No.: 219,853

[22] Filed: Dec. 23, 1980

Related U.S. Application Data

[62] Division of Ser. No. 131,824, Mar. 19, 1980, Pat. No. 4,315,923.

[51] Int. Cl.$^3$ .............................................. C08B 37/10
[52] U.S. Cl. .................................................... 536/21
[58] Field of Search ......................................... 536/21

[56] References Cited

U.S. PATENT DOCUMENTS

| | | | |
|---|---|---|---|
| 2,587,924 | 3/1952 | Taylor et al. | 536/21 |
| 2,623,001 | 12/1952 | Sylven et al. | 536/21 |
| 2,884,358 | 4/1959 | Bush et al. | 536/21 |
| 3,262,854 | 7/1966 | Yasuda | 536/21 |
| 3,817,831 | 6/1974 | Mancilla et al. | 536/21 |
| 3,862,003 | 1/1975 | Okuyama et al. | 536/21 |
| 4,122,250 | 10/1978 | Schmer | 536/21 |
| 4,192,916 | 3/1980 | Melby et al. | 536/21 |
| 4,301,153 | 11/1981 | Rosenberg | 536/21 |

*Primary Examiner*—Johnnie R. Brown
*Attorney, Agent, or Firm*—Karl F. Ross; Herbert Dubno

[57] ABSTRACT

A heparin-enriched material capable of long-term storage and particularly adapted for use as a raw material in processes for the extraction of heparin is produced by storing the animal organ material for a period of 0.5 to 15 hours (preferably 4 to 6 hours) at a temperature of 10° to 50° C. (preferably 30° to 50° C.), then injecting steam to effect a heat treatment at a temperature between 75° and 100° C. The heat treatment precipitates heparin-containing aggregate which is filtered from the aqueous phase and dried to a dry substance content of 90 to 95%.

9 Claims, No Drawings

PROCESS FOR THE PRODUCTION OF HEPARIN-CONTAINING PARTICULATE PRODUCTS

CROSS REFERENCE TO RELATED APPLICATION

This application is a division of Ser. No. 131,824 filed Mar. 19, 1980, entitled "Process for the Production of Organ Extracts with High Heparin Content", now U.S. Pat. No. 4,315,923.

FIELD OF THE INVENTION

The present invention relates to a process for the production of a new type of heparin-containing raw material from animal organs, whereby the industrial production of heparin is considerably improved.

BACKGROUND OF THE INVENTION

Heparin—due to its anti-coagulant property—is an important drug. Its synthetic production has not been accomplished heretofore and thus the raw material for large-scale heparin production is invariably animal organs rich is heparin, such as the small intestine of pig, cattle, sheep and lung. The active ingredient content even of animal organs rich in heparin is only $10^{-2}$–$10^{-3}\%$ of their weight, i.e. extremely low. Separation of the small amount of active ingredient from the large mass of ballast matter in the raw material alone is problematic, but it is especially so if the accompanying materials change their properties, such as by decomposition during storage or transportation of the raw material.

Consequently, for economical industrial production, in addition to the obvious requirement of preserving the total heparin content of the organ until processing, it also essential that the physical, chemical and morphological properties of the inactive materials representing the main part of the organ should remain unaltered. Any change in the properties of the inactive materials may cause processing and purification problems in the course of the pharmaceutical processing (extraction, etc.) of the heparin-containing raw materials, which may render the economical production of a suitable end product impossible.

It is advisable to meet these requirements already in the course of preparation (collection and storage) of the raw material.

The importance of collecting and storing the heparin-containing raw materials is dealt with only by a few patent specifications, e.g. Hungarian Pat. No. 148 776 and No. 149 329 and by the U.S. Pat. No. 2,587,924, but even these deal with the matter in question only tangentially. The significance of suitably treating the raw materials during the organ collection and storage is understandable by taking into account the following generally known facts:

Living organs being in physiological balance contain heparin in various forms, mainly fixed to various proteins. When the animals are slaughtered, the physiological balance of the living organs and tissues is upset and the autolysis of the hydrolyzing, proteolytic enzymes of the surviving tissues begins immediately, resulting in the uncontrolled decomposition of the accompanying ballast materials, occasionally coupled with the decomposition of the active ingredient.

Upon the collection and storage of the animal organs—usually taking place under unsterile circumstances—microbiological contamination can occur, as a result of which protein and active ingredient decomposing enzymes are released. Their effects are identical.

U.S. Pat. No. 2,884,358 (col. 1, lines 51–53) refers to the unpleasant odor arising during storage of the animal organs, the discoloration affecting the end product, pyrogenicity sets in, and the extraction is reduced.

Three methods have gained general acceptance for the collection and storage of heparin-containing organs:

(1) Quick frozen and deep frozen storage of the organs in natural state;

(2) Quick frozen and deep frozen storage of the organs after heat denaturation (where the denaturation is generally preceded by grinding and addition of water); and (3) Preservation of the water-diluted ground product of the organs (in case of mucosa without grinding, but after partial dewatering of the diluted watery suspension derived in the course of gut cleaning) with chemicals, generally with various inorganic salts.

A disadvantage of methods (1) and (2) is that they are energy-, investment- and labor-intensive. Attaining the temperature of $-18°$ C. ($0°$ F.) at a fast rate and holding it during the storage then during delivery until the commencement of processing necessitate the high energy- and investment demand. The labor cost is a result of the high labor force capacity tied up in the handling of the organs with high water content (77 to 85%), packing, delivery and preparation of the product (grinding in frozen state). The third method, i.e. the preservation with chemicals, is undoubtedly less energy-intensive than the former ones, but due to the high water content of the collected material (86–90%), the delivery volume and cost are considerably increased.

Disadvantages of the collection methods is eliminated by the method most realizable in the practice, whereby the fresh organ is processed to heparin continuously at the place of origin, or to an easily storable product. Similarly a satisfactory solution is the instant drying of the fresh organs (dewatering with solvent by drying through freezing or pulverization) and processing of the so-obtained more stable powder after storage. However, the application of these methods seemed to be feasible only under laboratory circumstances due to economic reasons (high cost of solvent, or high investment and running costs). (Methods of Biochemical Anal.: Vol. 24, page 244, 1977; Methods of Biochemical Anal.: Vol. 7, page 269; Methods of Carbon Chem.: Vol. 7, page 90, 1976).

OBJECTS OF THE INVENTION

An object of the invention is to provide a raw material from which heparin can be obtained on an industrial scale and in a continuous system, which enables the optimal utilization of the heparin-containing material.

Another object is to provide a process for the simultaneous removal of inactive materials present in the animal organs (fat, inorganic salts, polypeptides, nucleotides, nucleocytes, etc.), thus ensuring high concentration of the active ingredient content, thereby producing a heparin product whose chemical, physical, morphological composition is constant.

DESCRIPTION OF THE INVENTION

According to the invention a new heparin-enriched product is obtained. Stored at ambient temperature it preserves its composition for an unlimited period without the need for special conditions, including the germ number which is very low under the applied conditions.

From the new type of raw material an end product of therapeutic quality is producible by any known industrial heparin extraction method in such a manner, that—owing to the unchanged composition, high heparin content and small amount of accompanying material and low fat content—processing technologies can be optimalized in a higher degree.

Due to the form of the new raw material of a definite grain size range with large grain surface, amorphous, coherent even in wet medium, further advantages are attainable in the so-called extraction phase of the industrial heparin production (possibility of counterflow extraction).

The material according to the invention is produced, starting from animal organs, by storing the heparin-containing animal organs—if necessary after cutting them up—in a wet medium within the 10°–50° C. temperature range for 0.15–15 hours. Then a heparin-protein containing complex insoluble in water is separated from the pretreated suspension at a temperature between 75° and 100° C., which complex is transformed to well filterable aggregates by further heat treatment. The flocculated precipitation is separated and the isolated heparin-containing raw material is dried at 100° C. temperature until the 90–95% dry substance content is reached and a friable product is obtained.

The initial raw material is preferably pig's small intestine, mucosa, seroza, cattle lung, but every other heparin-containing organ, such as small intestine of cattle, sheep, cattle spleen, other entrails, liver etc. may be used for this purpose. When mucosa is used, the cutting and watery dilution are not necessary.

The other animal organs are cut up to 4–6 mm size and an aqueous suspension is prepared, which includes the heparin and proteins to various degrees in solution and also in the form of colloidal solution.

The aqueous suspension is set to 1.5–17% dry substance content. The dilution is carried out with water preferably of a temperature of 36°–42° C. Thus the external heating at the pretreatment is not necessary or is required only to a low degree. The obtained suspension starting out from the usual heparin-containing materials is pretreated in the temperature range of 30° to 50° C. generally for 2 to 6 hours.

After pretreatment, precipitation of the heparin-protein complex is carried out with instant direct steam blowing or with heat treatment for a longer period, while the main part of the heparin is fixed to the filterable proteins.

The heat treatment is carried out in a continuous system at over 85° C. for a minimum of 2 minutes and for 15 minutes, or longer in an intermittent system.

By precipitation of the proteins a favorable grain size is obtained in respect of the filtration-isolation, and the virulent germs are also destroyed at the same time.

The precipitation is isolated with about 20–25% dry substance content in a mechanical separator functioning by gravity. The mechanical separator should have a continuously regenerating filter surface, but continuous or intermittent flat sieves, curved sieves, centrifuges and worm separators are also applicable. The discharged filtrate may contain 5–35% of the original dry substance content, and depending on the controlled pretreatment is composed of nonheat-denaturable proteins, peptides, nucleic acid-derivatives, fats, lipoids, mineral salts. The isolated heparin concentrate is dried in a drier at 100° C.

temperature to 90–95% dry substance content. Thus a fat-deficient concentrate is produced, mostly between 0.2–1.6 mm grain size, in the form of amorphous particles of large surface, storable for a long period, which is particularly suitable for instance for intermittent or continuous counterflow extraction.

It has been found and experimentally demonstrated (See Example 1 below), that among the protein components of the fresh heparin-containing organs a large surplus of such proteins in relation to the natural heparin content can be found; these proteins are able to fix the dissolved heparin and heparin-protein complexes in a manner that they are isolated from the solution after the conventional irreversible heat denaturation. The amount of these proteins suitable to fix the heparin decreases as a function of the rate and time of autolysis (decomposition) since the surplus proteins capable to fixing are decomposed to polypeptide fractions not denaturating the heat and which are unsuitable for fixing.

Furthermore it has been found (see Example 2), that with the use of the controlled and checked short autolysis in the fresh organs, the amount of both the surplus heparin-fixing proteins and other proteins is reducible by breaking them down to units not denaturable by the heat effect, and in this way richer heparin basic material is obtainable by comparison with the natural initial materials after denaturation with the heat treatment.

The experiments led to surprising and unexpected results in which the decomposition rate of the proteins suitable for fixing the heparin is substantially lower than that of the proteins incapable for fixing.

Also during the process of autolysis the removal of the nucleotides, nucleosides, etc., i.e. other accompanying, production-disturbing components is possible in the filtrate.

As a result of the joint application of these discoveries, the obtained material of 20–25% dry substance content, is a heparin-enriched material practically free of loss as far as the heparin is concerned, which in comparison with the natural raw materials and calculating in dry substance, contains 5–35% less accompanying material that disturbs the heparin extraction by techniques in which the heparin is dissolved by any of the usual extraction methods.

We have also found that the heat sensitivity of the derived raw material is lower than that of the heparin. Therefore the costly and careful drying methods, such as lyophilization, pulverized drying or dewatering with solvent, can be eliminated because the heparin-protein bond developed has such a protective effect on the heparin content, that the product can be kept at temperatures over 100° C. even for several hours.

Advantages of the process can be summed up as follows:

A new type of heparin concentrate with 90–95 weight % dry substance content is produced and is storable without change of the active ingredient content and composition at normal temperatures for long periods;

with respect to extraction of the heparin content, it enables optimal yield calculated per animal organ unit;

the necessary processes are readily animal organ processing machine group, representing low specific space-, energy- and investment demand;

the germ number of the heparin-containing concentrate is low, containing small amount of lipoids and fat;

the consistency and grain size of the new raw material is the most favorable in respect of the further processing technology, the heparin isolated to the heat effect, fixed to the native proteins is easily mobilized, i.e. can be dissolved again;

the constant composition of the heparin-containing raw material concentrate offers favorable possibility for the simplification and optimalization of the complete processing technology; and the long distance transportation of the raw material is economical.

According to a feature of the invention, the heparin-containing animal organ—if necessary—is cut up in industrial meat grinder to 4-6 mm grain size according to the rate of slaughtering and derivation. The animal organ is diluted with water (at a temperature of 18°-50° C. up to 1.5-17% concentration. The wet organ suspension is delivered by a pump into the equipment used for the preliminary autolysis and it is held at a temperature of 30° to 50° C. for 2-6 hours. After pretreatment the organ suspension is subjected to heat treatment at a temperature of 82° to 100° C. An instant steam injector is used for the heat treatment. The heparin-containing precipitate in the form of easily filterable friable grains are obtained from the aqueous suspension of the organ kept in continuous motion in an insulated pipe section at a slow flow rate for 2-6 minutes. The wet medium—containing only inactive disturbing materials—is removable from the friable precipitate by gravity, for instance through sieves, and the raw material is obtained in the form of at least 23% dry substance content. The filtration is carried out in the filter unit of an apparatus ensuring a constantly regenerating effective filter surface; thus the fat extraction, etc., is more effective than the intermittent systems and efficiency can be even further increased by a built-in washing system.

The isolated raw material can be stored without cooling and freezing, if the wet raw material is continuously dried at the rate of derivation in the highly efficient drying unit of the equipment described.

During drying the temperature of both the steam and air as well as that of the humid air leaving the equipment is regulated in such a way that a heparin concentrate corresponding to the 0.2-1.6 mm grain size of about 92% dry substance content is obtained during a relatively short drying period between the 80°-180° C. inlet and 50°-110° C. outlet air temperature limits.

This concentrate is enzyme-deficient, it is of constant composition, with low germ number, fat-deficient, preserving its unchanged composition in the industrially calculated temperature range for a long period, its low germ number does not allow the germ propagation, it is economically storable and the transportable. The heparin content of the obtained concentrate—depending on the heparin content of the initial organ—varies. Starting out from the mucous membrane of the pig, a product of 0.15 kg/$10^5$NE active ingredient is obtained, which contains substantially less ballast material in comparison with the other heparin basic materials. The heparin can be brought into aqueous solution from the obtained concentrate with any of the conventional extraction methods under more favorable conditions in relation to the basic material used so far.

SPECIFIC EXAMPLES

Further details of the invention are described in the following examples:

EXAMPLE 1

This Example demonstrates that concentration of the heparin-fixing proteins present in the fresh animal organs is higher than that of the heparin.

1.0 kg fresh mucosa of the pig's small intestine with 16.0 weight % dry substance content is diluted with 1.0 liter water. Powdery, pure heparin was dissolved in the diluting water by setting the heparin concentration to 82 NE/ml (NE=international unit). The suspension was heated to 85° C. during mixing, then the heat denaturated organ was separated in a sieve after a rest for 5 minutes. On the basis of the sample obtained from the 1380 ml filtrate, it was established that the heparin concentrate is 1.4 NE/ml, i.e. about 80,000 NE of the admitted 82,000 NE heparin was fixed to the denaturated animal organ.

If the mucous membrane of the fresh small intestine of pig is kept at room temperature for 1½ day, and diluted with 1.0 liter water per 1.0 kg, the heparin concentration of which is 41 NE/ml, finally the heat denaturation is carried out at 85° C., then it is found that the heparin concentrate of the 1440 ml filtrate is 2.1 NE/ml, i.e. the heparin fixing ability of the denaturated organ obtained at processing of the 1.0 kg mucous membrane of the pig's small intestine is reduced to 38,000 NE heparin after autolysis for one and a half day.

EXAMPLE 2

This example demonstrates that, by removal of the ballast materials of the organs, a raw material is producible without loss of heparin, provided that the decomposition rate of the organ-parts—indifferent in respect of the heparin-protein bond during the process of the preliminary autolysis—is higher than that of the proteins fixing the heparin by denaturation and isolating with subsequent filtration.

Each of the three samples of 2 kg fresh small intestine of pig with 17.3 weight % dry substance content was diluted with 3 liters of water. The temperature was set to 29.5° C. the first sample was processed without autolysis, the second one after 6, the third one after 18 hours autolysis. The processing was carried out by heating the organ suspension to 93° C. during mixing, then filtered after a rest for 5 minutes. Weight and dry substance content of the denaturated organs retained on the filter, as well as volume, dry substance content and heparin concentration of the discharged filtrate were measured.

Without autolysis 1.37 kg denaturated organ with 22.8% dry substance content was obtained from the 2 kg fresh pig's small intestine, the volume of filtrate was 3670 ml, dry substance content 0.82 weight %, heparin activity below the value of 1.25 NE/ml. After autolysis for 6 hours weight of the denaturated organ was 1.18 kg, dry substance content 23.2%, volume of filtrate 3780 ml, dry substance content 1.72%, heparin activity 1.25 NE/ml. From the mucosa of the 2 kg pig's small intestine after autolysis for 18 hours 0.99 kg denaturated organ was obtained with 24.1% dry substance content, volume of filtrate 3980 ml, dry substance content 2.43%, heparin activity below the value of 1.25 NE/ml.

Since no loss of heparin appeared during the treatments, the heparin content of the initially used organ was 118,000 NE, thus more heparin concentrated raw material was producible.

The result of the processing is shown in Table 1, as follows:

TABLE 1

| Initial material and processing method | Weight of wet organ g | Dry substance content % | Total dry substance content g | Total heparin content NE | Heparin content NE/g dry substance |
| --- | --- | --- | --- | --- | --- |
| untreated intestine | 2000 | 17.3 | 346 | 118 000 | 342 |
| denaturated intestine | 1370 | 22.8 | 312 | 118 000 | 380 |
| intestine after 6 h autolysis, but denaturated | 1180 | 23.2 | 274 | 118 000 | 434 |
| intestine after 18 h autolysis, but denaturated | 990 | 24.1 | 238 | 118 000 | 500 |

EXAMPLE 3

This example demonstrates that the mucosa of the pig's small intestine is driable in the intermittent system without loss after denaturation.

260 kg wet mucosa of pig's small intestine with 6.4% dry substance content derived from the gut cleaning machine is collected in homogenized condition. 10 kg sample is taken for the further comparative tests (sample A), then the composite is heated during mixing to 85° C. within a short time in a device suitable for the direct admission of steam. Approaching the final temperature, the extent of mixing was reduced. After reaching 85° C., the composite was rested for 15 minutes whereby the denaturation process was completed.

The material coagulated in the form of friable precipitation was carried from the device onto metal sieves with 1.2 mm mesh size, and yellowish heparin-containing coagulating grains were separated. After filtration, the filtered material was rested for 1 hour, while it was mixed over several times to intensify the dewatering. 62 kg heparin-containing coagulated material was obtained with relatively less fat content than that of the original, initial material, although a certain part of the fat is fixed again on the large surface of the precipitation during the filtration process. Dry substance content of the coagulated product: 23.4%.

Heparin activity of the sample taken from the filtrate is below the 0.9 NE/ml value, dry substance content 0.88%. On the basis of the composition it was found to contain fat, insoluble and soluble proteins, some peptides and polypeptides, inorganic salts and some other inert components.

10 kg denaturated samples B, C and D were taken from each of the processed initial materials.

Sample B was compressed in filter press to a 1.5 cm layer thickness. As a result of the pressing 7.4 kg product with 30.3% dry substance content was produced. If the layer used at the pressing is thicker, then the pressing efficiency will become lower.

Sample C was divided into two equal parts (samples $C_1$ and $C_2$). Sample $C_1$ of 0.5 cm layer thickness was dried in a ventilated desiccator at 90° C. for 1½ day. 1.31 kg product with 88% dry substance content was obtained, cut up by grinder and marked with $C_{11}$ hereinafter. The other part of sample C was not dried, this is sample $C_2$.

Parallel extraction experiments were conducted with samples A, $C_2$ and $C_{11}$ for comparative tests in respect of the extractable heparin content.

In the interest of facilitating the numerical comparison, the quantity processed from each sample corresponded to 468 kg dry substance content. Accordingly 7.31 kg of sample A, 2.0 kg of sample $C_2$ and 5.32 kg of $C_{11}$ were processed.

For uniformity of the comparative extraction processes identical dry substance concentration and reagent ratios were set in. The extraction composition was diluted with tap water to 8.0 liter, for which purpose 690 ml tap water in case of sample A, 6000 ml in case of sample $C_2$ and 7470 ml in case of sample $C_{11}$ were necessary.

The further operative steps of the extraction were the following:

385 g ammonium sulphate was added to the aqueous composition during constant mixing, then heated to 60° C. At this temperature 10.0 pH value was set with the use of sodium hydroxide and in order to adjust the extraction balance, the former temperature was held for 2.5 hours. After 2.5 hours during constant mixing the pH value was reduced to 8.2 by adding solid ammonium chloride, then the composition was heated to boiling point. After boiling for 5 minutes, the composition was rested for 10 minutes, then organ residue was separated from the extraction liquid on framed metal sieve of 1.0 mm mesh size. A sample was taken from the organ residue retained on the filter, the dry substance content was measured in order to determine the amount of extraction liquid present in the organ residue. The yields calculated on the basis of the heparin content found in the samples and according to the original initial weight were the following:

| Sample A | |
| --- | --- |
| heparin content | 126,000 NE |
| proportion of material | 58.2 kg organ/MNE |
| | (MNE = million international unit) |
| Sample $C_2$ | |
| heparin content | 148,000 NE |
| material proportion | 13.5 kg organ/MNE |
| Sample $C_{11}$ | |
| heparin content | 162,000 NE |
| material proportion | 3.27 kg organ/MNE |

The comparative analysis of above results is given in Table 2 following Example 4.

EXAMPLE 4

The small intestine mucosa of 6.3% average dry substance content derived on the gut cleaning machine according to Example 3, is passed through an insulated pipe section with delivery pump. 1.5 hour dwelling period is set at 41° C. in the equipment.

The autolysed raw animal organ was processed in a continuous system (see Ser. No. 097,969 filed Nov. 28, 1979, now U.S. Pat. No. 4,276,701). In the instant heater unit the organ composite was heated to 90° C. by the direct admission of steam, then treated at gentle flow for 7.5 minutes in a spiral heat insulated pipe section pertaining to the equipment. The coagulated grains were separated with a delivery spiral type filter drum with a closed vapor space. The delivery spiral type filter drum ensures delivery of the filtered heparin-containing raw material from the filter unit at continuous filtration.

The filtered product is delivered through a feeder system into the horizontally arranged cylindrical equipment connected to the filters, heated externally with steam, internally with hot air, and provided with mixer and rollers. The continuous drying of the product in this equipment is carried out in such a way that the hot air is produced in separate air heating unit in which the air sucked in from the surroundings by fan is steam heated to 142° C. The temperature of the outgoing wet air is set to 82°–88° C.

The initial raw material was admitted at the rate of 600 liter/hour and after running the equipment for 6 hours 178 kg nearly fatless product with 90.4% dry substance content and $10^2$–$10^3$ pc/g germ number was obtained. Grain distribution of the obtained product is such that it is storable at room temperature in undamaged condition for unlimited period, 80% of its grain size being 1.6–0.2 mm.

Samples were taken from the filtrate at every half an hour, the dry substance content, heparin content and important chemical components being tested. The average dry substance content was 1.41%, heparin activity below 0.92 NE/ml, the filtrate containing significant amount of fat, less insoluble and dissolved protein than the isolated filtrate in Example 11, but more peptides and polypeptides, as well as inorganic salts and inert impurities.

The product obtained as a result of autolysis, enables the production of heparin-enriched basic material. The dried raw material in the Example is sample E, processed by extraction in the quantities and proportions as given in Example 3.

Composition of the samples according to Examples 3 and 4 and results of the experiments are summed up in Table 2.

In the interest of accurate comparison two types of heparin content and three types of material proportion values were calculated. Calculation of the two types of heparin content is necessary because the applied extraction method was a single intermittent extraction, in which the organ residues retained on the sieve in various quantities during separation of the extraction liquids—assuming balance—contained extraction liquid of identical concentration with the filtered extraction liquid. It is noted, that this heparin content is theoretically obtainable with repeated extraction. The value shown in column 9 is the actually obtained value calculated on the basis of the value of the filtered extract liquids, while the so-called theoretical values given in colum 13 represent the theoretically obtainable heparin contents calculated by taking into account the extract liquid content of the organ residue. The extract liquid content of each organ residue is shown in column 12 of the Table. On the basis of these values it can be laid down that by increasing the dry substance content of the basic material to be processed, the extraction content of the organ residue is reduced, i.e. the extraction process can be realized more effectively from the basic material with higher dry substance content even in case of multiple extractions. The materials proportion values given in column 10 of the Table were calculated on the basis of the actual weight shown in column 6 and according to the obtained heparin content shown in column 9. The values calculated in column 11 represent the data related to the 100% dry substance content (column 6) of the former ones. The so-called material proportion values calculated in column 11 correspond to the values related to the 100% dry substance content (column 6) based on the theoretical heparin content (column 13). On the basis of the data of columns 6 and 13 the heparin content of products extractable with given method, obtained with and without autolysis can be compared. According to the conclusion drawn from the Table, the material proportion value of the denaturated and dried products is nearly identical in the products processed without autolysis and in comparison with pig's raw small intestine mucosa it is about 10% more favorable. During the denaturation process several inert materials can be removed with the filtrate. with the filtrate. In case of preliminary autolysis enrichment of the heparin content is much higher—about 30%—in comparison with the fresh organ.

The Tables lead to the conclusion that the heparin content of the denaturated-dried raw material obtained via autolysis calculated to identical dry substance content is significantly higher, than that of the heparin basic material processed without autolysis. The comparative experiments prove that the drying does not cause deterioration of the heparin.

The obtained new type of raw material is processible with optional conventional extraction method to such heparin product, from which end-product of therapeutic quality is producible.

TABLE 2

| 1 Symbol of sample | 2 Type of material | 3 Preliminary autolysis | 4 Dry substance % | 5 Processed qty kg | 6 Processed dry sub. g | 7 Extraction liquid vol. ml | 8 Extraction liquid con. cont. NE/ml | 9 Extraction liquid hep. cont. NE | 10 Proportion of material for orig. wei. kg/NME | 11 Proportion of material for 100% organ kg/MNE | 12 Extract. liquid content of organ residue ml | 13 Theoritical hept. cont. NE | 14 Theoritical material proportion for 100% organ kg/MNE |
|---|---|---|---|---|---|---|---|---|---|---|---|---|---|
| A | raw mucosa | — | 6.4 | 7.31 | 468 | 6120 | 20.6 | 126000 | 58.2 | 3.72 | 1740 | 162000 | 2.89 |
| C$_2$ | denat. mucosa | — | 23.4 | 2.0 | 468 | 6000 | 22.5 | 148000 | 13.5 | 3.16 | 1340 | 179500 | 2.62 |
| C$_{11}$ | denat. dried mucosa | — | 88.0 | 0.532 | 468 | 7030 | 23.1 | 162500 | 3.27 | 2.88 | 860 | 182000 | 2.57 |
| E | denat. | — | 90.4 | 0.518 | 468 | 7120 | 28.6 | 204000 | 2.54 | 2.29 | 900 | 229000 | 2.04 |

TABLE 2-continued

| 1 Symbol of sample | 2 Type of material | 3 Preliminary auto-lysis | 4 Dry substance % | 5 Processed qty kg | 6 Processed dry sub. g | 7 Extraction liquid vol. ml | 8 Extraction liquid hep. cont. con-cont. NE/ml | 9 Extraction liquid hep. cont. NE | 10 Proportion of material for orig. wei. kg/NME | 11 Proportion of material for 100% organ kg/MNE | 12 Extract. liquid content of organ residue ml | 13 Theoretical material in proportion hept. cont. NE | 4 Theoretical material in proportion or 100% organ kg/MNE |
|---|---|---|---|---|---|---|---|---|---|---|---|---|---|
| | dried mucosa | | | | | | | | | | | | |

What we claim is:

1. Process for producing a heparin-enriched raw material capable of long-term storage to recover heparin therefrom, said process comprising the steps of:
   (a) storing heparin-containing animal organ material in an aqueous medium at a temperature of substantially 10° to 50° C. for a preriod of substantially 0.5 to 15 hours;
   (b) thereafter heat-treating the composition of step (a) at a temperature of 75° to 100° C. to precipitate a heparin-protein complex insoluble in water from the aqueous phase in the form of a readily filterable aggregate;
   (c) filtering said aggregate from the aqueous phase; and
   (d) drying said aggregate to produce a friable coherent particulate product with a 90 to 95% by weight dry substance content.

2. The process defined in claim 1 wherein the animal material treated in step (a) is heparin-containing animal organs, further comprising the step of cutting up said organs to a particle size of substantially 4 to 6 mm.

3. The process defined in claim 1 wherein the animal material of step (a) is stored in a suspension having substantially 1.5 to 17% dry substance content.

4. The process defined in claim 1 wherein the treatment in step (a) is carried out at a temperature of 30° to 50° C. for a period of 4 to 6 hours.

5. The process defined in claim 4 wherein the treatment in step (b) is carried out by instantaneously heating a suspension derived from step (a) to a temperature between 75° and 100° C. and thereafter maintaining the temperature in the latter range for a period of 12 to 15 min.

6. The process defined in claim 5 wherein the treatment in step (b) is carried out by injecting steam into the suspension derived from step (a).

7. The process defined in claim 6 wherein, the step (c), the product obtained has a dry substance content of 20 to 25%.

8. The process defined in claim 7 wherein step (c) is carried out in a gravity-separating mechanical separator with closed-vapor system and a regenerated filter surface.

9. The process defined in claim 8 wherein the drying step (d) is carried out in a continuous drier.

* * * * *